United States Patent
Ikeda

[11] Patent Number: 6,131,226
[45] Date of Patent: *Oct. 17, 2000

[54] 1,4-DIHYDROPYRIDINE COMPOUNDS AS BRADYKININ ANTAGONISTS

[75] Inventor: Takafumi Ikeda, Handa, Japan

[73] Assignee: Pfizer Inc., New York, N.Y.

[ * ] Notice: This patent is subject to a terminal disclaimer.

[21] Appl. No.: 09/125,137

[22] PCT Filed: Jan. 27, 1997

[86] PCT No.: PCT/IB97/00058

§ 371 Date: Feb. 1, 1999

§ 102(e) Date: Feb. 1, 1999

[87] PCT Pub. No.: WO97/30048

PCT Pub. Date: Aug. 21, 1997

[30] Foreign Application Priority Data

Feb. 19, 1996 [WO] WIPO ............... PCT/IB96/00132

[51] Int. Cl.[7] ............... A61K 31/495; A61K 31/4436; A61K 31/439; C07D 401/06; C07D 403/06

[52] U.S. Cl. ............... 14/252.13; 514/253.01; 514/253.03; 514/253.04; 544/333; 544/362; 544/365

[58] Field of Search ............... 544/365, 362, 544/333; 514/252, 255, 256, 252.13, 253.01, 253.03, 253.04

[56] References Cited

U.S. PATENT DOCUMENTS 5,859,011  1/1999  Ito et al. .................. 514/252
5,861,402  1/1999  Ikeda ..................... 6514/252

Primary Examiner—Alan L. Rotman

Attorney, Agent, or Firm—Peter C. Richardson; Paul H. Ginsburg; Roy F. Waldron

[57] ABSTRACT

A compound of formula (I) and its pharmaceutically acceptable salts, wherein $A^1$ and $A^2$ are each halo; X is direct bond, $CH_2$, CO, O, S, S(O) or $S(O)_2$; $R^1$ is selected from a variety of groups such as hydrogen; substituted or unsubstituted $C_{1-4}$ alkyl; substituted or unsubstituted piperidinyl; substituted or unsubstituted $C_{5-14}$ cycloalkyl, bicycloalkyl or tricycloalkyl; substituted or unsubstituted $C_{7-14}$ azacyclo-, azabicyclo- or azatricyclo-alkyl; bicyclo $C_{7-10}$ alkenyl; benzocyclo $C_{5-7}$ alkyl; and heterocyclic; $R^2$ is hydrogen, $C_{1-4}$ alkyl, substituted or unsubstituted phenyl or heterocyclic; and $R^3$ and $R^4$ are each $C_{1-5}$ alkyl. The novel dihydropyridine compounds of this invention have excellent bradykinin antagonistic activity and are thus useful for the treatment of inflammation, cardiovascular disease, pain, common cold, allergies, asthma, pancreatitis, burns, virus infection, head injury, multiple trauma or the like in mammalian, especially humans.

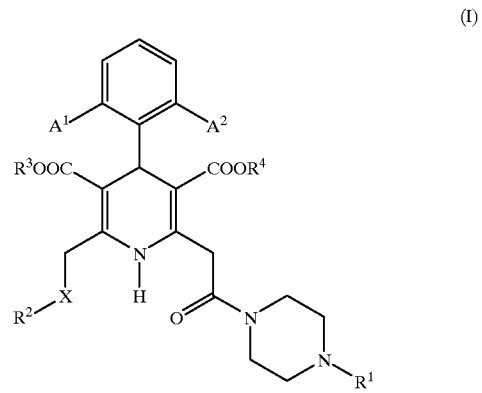

8 Claims, No Drawings

1,4-DIHYDROPYRIDINE COMPOUNDS AS BRADYKININ ANTAGONISTS

This application is the U.S. national stage Section 371 of International application No. PCT/IB96/00058, filed Jan. 27, 1997, which claims the priority of International application No. PCT/IB96/00132, filed Feb. 19, 1996.

TECHNICAL FIELD

This invention relates to novel 1,4-dihydropyridine compounds, and more particularly to 1,4-dihydropyridine compounds having a substituted or unsubstituted-carbamoylmethyl group attached to the 2-position of the dihydropyridine ring. These compounds are useful as antagonists of bradykinin, and are thus useful in the treatment of inflammation, cardiovascular disease, pain, common cold, allergies, asthma, pancreatitis, burns, virus infection, head injury, multiple trauma or the like in mammalia, especially humans. The present invention also relates to a pharmaceutical composition useful in the treatment of the above clinical conditions, which comprises the 1,4-dihydropyridine compound of the invention and a pharmaceutically acceptable carrier.

BACKGROUND ART

Bradykinin ("BK") is generated under normal conditions in mammalia by the action of various plasma enzymes such as kallikrein on high molecular weight kininogens. It is widely distributed in mammals, as are its two receptor subtypes, $B_1$ and $B_2$. The actions of BK at the B. receptor include mainly contraction of arterial and venous preparations, although it can cause relaxation of peripheral resistance vessels as well.

Many of the more important functions of BK, such as increases in vascular permeability, pain, and vasodilatation, however, are mediated by the $B_2$ receptor. These effects at the $B_2$ receptor are believed to be responsible for BK's role in numerous diseases, such as inflammation, cardiovascular disease, pain, and the common cold. Hence antagonists at the $B_2$ receptor should find considerable therapeutic applications. Most of the efforts in this area thus far have been directed at peptidic analogues of the BK structure, some of which have been studied as analgesics and antiinflammatory agents.

It would be desirable if there were provided a non-peptide antagonist of the $B_2$ receptor, having a good $B_2$ antagonistic activity and a good metabolic stability.

BRIEF DISCLOSURE OF THE INVENTION

The present invention provides a compound of the formula:

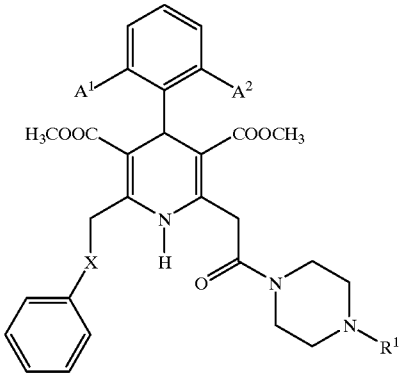

and its pharmaceutically acceptable salts, wherein
$A^1$ and $A^2$ are each halo; X is CO, S(O)$_2$ or S(O)—(CH$_2$)n wherein S atom is directly attached to the phenyl and n is 0, 1 or 2 (preferably n is 0); and $R^1$ is 8-azabicyclo[3.2.1]octyl, quinuclidinyl, bicyclo[3.3.0]octyl, $C_{3-10}$ cycloalkyl, 2,3,5,6-tetrahydro-4H-thiopyranyl or $C_{3-6}$ cycloalkyl-$C_{1-4}$ alkyl, optionally substituted with $C_{1-4}$ alkyl, hydroxy, dioxolanespiro or oxo.

The dihydropyridine compounds of this invention have excellent bradykinin antagonistic activity and are thus useful for the treatment of medical conditions caused by bradykinin such as inflammation, cardiovascular disease, pain, common cold, allergies, asthma, pancreatitis, burns, virus infection, head injury, multiple trauma or the like in mammalia, especially humans.

The present invention also provides a pharmaceutical composition for the treatment of inflammation, cardiovascular disease, pain, common cold, allergies, asthma, pancreatitis, burns, virus infection, head injury, multiple trauma or the like, which comprises a therapeutically effective amount of the dihydropyridine compound of formula (1) or its pharmaceutically acceptable salt together with a pharmaceutically acceptable carrier.

The present also provides a method for the treatment of disease conditions caused by bradykinin, in a mammalian subject, which comprises administering to said subject a therapeutically effective amount of a compound of formula (1).

DETAILED DESCRIPTION OF THE INVENTION

Preferably, $A^1$ and $A^2$ are chloro.
Preferably, $R^1$ is 8-methyl-8-azabicyclo[3.2.1]oct-3-yl, quinuclidin-3-yl, 3-hydroxy-bicyclo[3.3.0]oct-7-yl, [1-(hydroxy) cyclopentyl]ethyl or 3-oxo-bicyclo[3,3,0]oct-7-yl.

Among the dihydropyridine compounds of this invention, preferred individual compounds are:
dimethyl 4-(2,6-dichlorophenyl)-2-[4-(8-methyl-8-azabicyclo[3.2.1]oct-3-yl)-1-piperazinyl] carbonylmethyl-6-phenylsulfinylmethyl-1,4-dihydropyridine-3,5-dicarboxylate dihydrochloride;
dimethyl 4-(2,6-dichlorophenyl)-2-[4-(8-methyl-8-azabicyclo[3.2.1]oct-3-yl)-1-piperazinyl] carbonylmethyl-6-(2-oxo-2-phenylethyl)-1,4-dihydropyridine-3,5-dicarboxylate dihydrochloride;
dimethyl 4-(2,6-dichlorophenyl)-(2-oxo-2-phenylethyl)-2-[4-(3-quinuclidinyl)-1-piperazinyl]carbonylmethyl-1,4-dihydropyridine-3,5-dicarboxylate dihydrochloride;

dimethyl 4-(2,6-dichlorophenyl)-(2-oxo-2-phenylethyl)-2-[4-(3-hydroxy-bicyclo[3.3.0]oct-7-yl)piperazin-1-yl]carbonylmethyl-1,4-dihydropyridine-3,5-dicarboxylate hydrochloride;

dimethyl 4-(2,6-dichlorophenyl)-2-{2-[1-(hydroxy)cyclopentyl]ethylpiperazinyl} carbonylmethyl-6-phenylsulfinylmethyl-1,4-dihydropyridine- 3,5-dicarboxylate;

dimethyl 4-(2,6-dichlorophenyl)-2-[4-(8-methyl-8-azabicyclo[3,2,1]octan-3-yl)-1-piperazinyl]carbonylmethyl-6-(phenylsulfinylmethyl-1,4-dihydropyridine-3,5-dicarboxylate dihydrochloride;

dimethyl 4-(2,6-dichlorophenyl)-2-[4-(3-hydroxy-bicyclo[3,3,0]oct-7-yl)-1-piperazinyl]carbonylmethyl-6-phenylsulfinylmethyl-1,4-dihydropyridine-3,5-dicarboxylate monohydrochloride;

dimethyl 4-(2,6-dichlorophenyl)-2-[4-(3-oxo-bicyclo[3,3,0]oct-7-yl)piperazinyl]-carbonylmethyl-6-phenylsulfinylmethyl-1,4-dihydropyridine-3,5-dicarboxylate, monocitric acid;

dimethyl 4-(2,6-dichlorophenyl)-2-[4-(cis-1,5-dimethyl-3-oxo-bicyclo[3,3,0]oct-7-yl)-piperazinyl]carbonylmethyl-6-phenylsulfinylmethyl-1,4-dihydropyridine-3,5-dicarboxylate, monohydrochloride; and dimethyl 4-(2,6-dichlorophenyl)-2-[4-(5-oxo-cyclooctyl)-piperazinyl]carbonylmethyl-6-phenylsulfinylmethyl-1,4-dihydropyridine-3,5-dicarboxylate, monohydrochloride.

Among these compounds, the more preferred compounds are:

dimethyl 4-(2,6-dichlorophenyl)-2-[4-(8-methyl-8-azabicyclo[3.2.1]oct-3-yl)-1-piperazinyl]carbonylmethyl-6-phenylsulfinylmethyl-1,4-dihydropyridine-3,5-dicarboxylate dihydrochloride;

dimethyl 4-(2,6-dichlorophenyl)-2-[4-(8-methyl-8-azabicyclo[3.2.1]oct-3-yl)-1-piperazinyl]carbonylmethyl-6-(2-oxo-2-phenylethyl)-1,4-dihydropyridine-3,5-dicarboxylate dihydrochloride;

dimethyl 4-(2,6-dichlorophenyl)-(2-oxo-2-phenylethyl)-2-[4-(3-quinuclidinyl)-1-piperazinyl]carbonylmethyl-1,4-dihydropyridine-3,5-dicarboxylate dihydrochloride; and dimethyl 4-(2,6-dichlorophenyl)-(2-oxo-2-phenylethyl)-2-[4-(3-hydroxy-bicyclo[3.3.0]oct-7-yl)piperazin-1-yl]carbonylmethyl-1,4-dihydropyridine-3,5-dicarboxylate hydrochloride.

Among these compounds, the most preferred compounds are:

dimethyl 4-(2,6-dichlorophenyl)-2-[4-(8-methyl-8-azabicyclo[3.2.1]oct-3-yl)-1-piperazinyl]carbonylmethyl-6-phenylsulfinylmethyl-1,4-dihydropyridine-3,5-dicarboxylate dihydrochloride; and dimethyl 4-(2,6-dichlorophenyl)-2-[4-(8-methyl-8-azabicyclo[3.2.1]oct-3-yl)-1-piperazinyl]carbonylmethyl-6-(2-oxo-2-phenylethyl)-1,4-dihydropyridine-3,5-dicarboxylate dihydrochloride.

General Synthesis

The dihydropyridine compounds of formula (1) of this invention may be prepared by a variety of synthetic methods known to those skilled in the art. For example, the dihydropyridine compounds of formula (1) may be prepared by reaction of compound (II) with compound (D), followed, if desired, by conversion of a compound in which $R^1$ is H into a compound in which $R^1$ is other than H, as indicated in the following Preparation Method A.

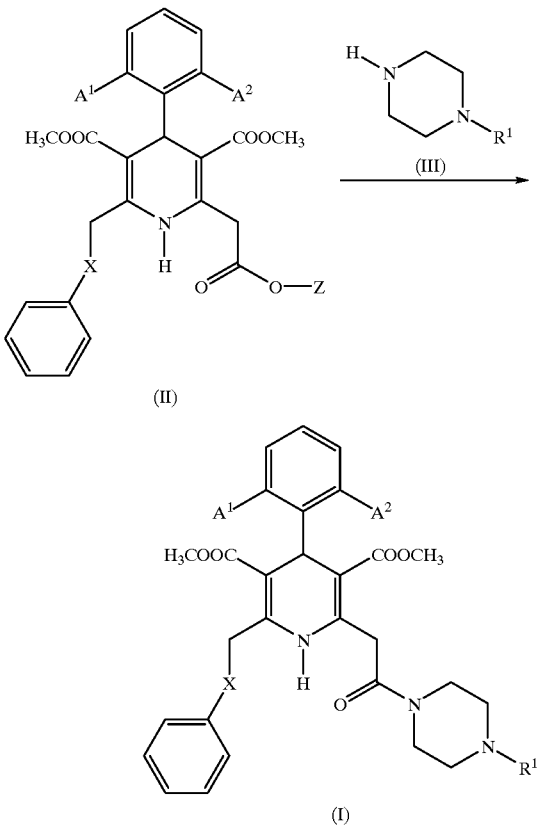

Preparation Method A:

(wherein Z is hydrogen or lower alkyl such as methyl and ethyl; and the other symbols are as already defined, with proviso that X is protected carbonyl, sulfide or sulfoxide)

In Preparation Method A, when Z is lower alkyl, the compound (II) may be first subjected to selective saponification of the ester residue at the 2-position of the compound (II), followed by acidification to afford a free acid, which is coupled with the piperazine compound (II) to give the dihydropyridine compounds (I). When Z is H, the compound (II) may be directly coupled with the piperazine compound (III) to obtain the dihydropyridine compounds (I). In this case, when X is carbonyl in the final compound, the carbonyl may be protected by a conventional protecting group which is removed in a later step by conventional means. A suitable protecting group for a carboxy group is, for example, a $C_{1-4}$ alkyl (especially methyl or ethyl) which may be removed by hydrolysis with a suitable base such as an alkali metal hydroxide (e.g., lithium or sodium hydroxide).

The selective saponification and the acidification may be carried out by conventional procedures. In a typical procedure, the selective saponification is carried out by treatment with 2N sodium hydroxide in aqueous methanol. In a typical procedure, the acidification is carried out by treatment with 1N hydrochloric acid in a suitable reaction-inert solvent.

The coupling reaction between the obtained acid and 4-N-substituted piperazine may be carried out in a reaction-inert solvent as listed above (preferably dichloromethane) using a coupling agent such as dicyclohexylcarbodiimide (DCC), water soluble carbodiimide (WSCD), 2-ethoxy-N-ethoxycarbonyl-1,2-dihydroquinoline, Bop agent (Benzotriazol-1-yloxy-tris(dimethylamino)phosphonium hexafluorophosphate), diethyl azodicarboxylate-triphenylphosphine, diethylcyanophosphonic acid and diphenylphosphorylazide. This reaction may be carried out at a temperature in the range from −30 to 40° C., usually from 0° C. to 25° C. for 10 minutes to 96 hours, usually 30 minutes to 24 hours.

A compound (I) can be obtained from the corresponding compound (I) wherein $R^1$ is H, by reductive alkylation of the terminal nitrogen with appropriate aldehyde or ketone. The reductive alkylation may be carried out in a suitable reaction-inert solvent, in the presence of a suitable reducing agent such as $NaBH_4$, $NaBH_3CN$ or $NaBH(OAc)_3$ at a temperature in the range from −20 to 120° C., usually 0 to 80° C. for 10 minutes to 1 week, usually 30 minutes to 96 hours, optionally in the presence of molecular sieves.

In addition, the 4-N-substituted piperazines (III) as used herein may be either known or may be prepared by known methods. For example, the 4-N-substituted piperazines may be prepared by means of (1) N alkylation of 4-N-protected piperazine with appropriate alkyl halide, $R^1$-halo, or (2) reductive amination of 4-N-protected piperazine with appropriate aldehyde or ketone in the presence of a reducing agent, followed by deprotection of the amino-protecting group. Suitable amino-protecting groups include, for example, benzyl, benzyloxycarbonyl and t-butoxycarbonyl group. Suitable reducing agents include, for example, sodium cyanoborohydride, aluminum-based reducing reagents, boranes, borohydrides or trialkylsilanes. After finishing introduction of a desired $R^1$ group, the amino-protecting group is removed by a suitable standard procedure to provide the objective compound.

The compound (II) may be prepared by several methods as indicated in the following Preparation Methods B-I to B-III.

Preparation Method B-I:

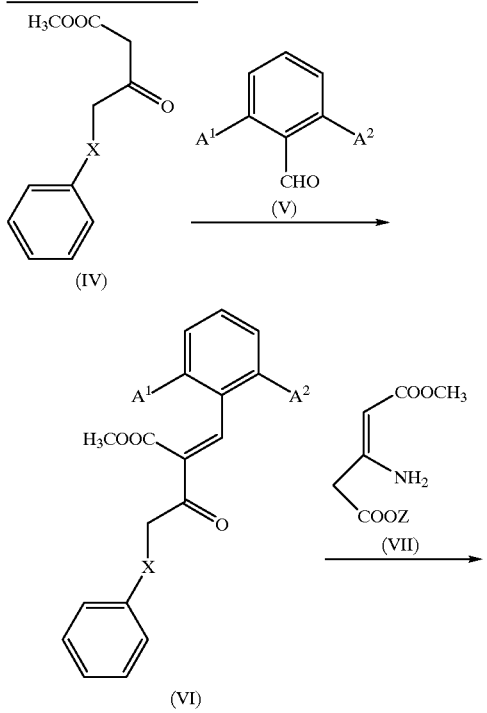

(IV)

(VI)

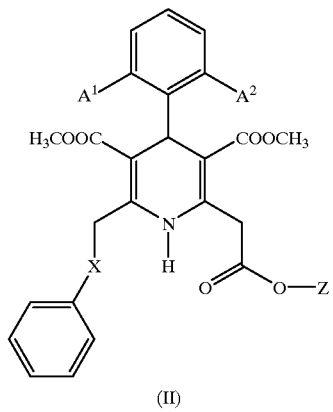

(II)

(Wherein all the symbols are already defined, with proviso that X is protected carbonyl, sulfide or sulfoxide)

This method utilizes the modified Hantzsch synthesis as described in A. Sausins and G. Duburs, *Heterocycles*, 1988, 27, 269. In this method, beta-keto ester (IV) is first reacted with substituted benzaldehyde (V) to obtain compound (VI). In this case, when X is carbonyl in the final compound, the carbonyl may be protected by a conventional protecting group which is removed in a later step by conventional means. A suitable protecting group for carbonyl group is, for example, a di- $C_{1-4}$ alkyl ketal (especially dimethyl or diethyl), or $C_{2-3}$ alkylene glycol ketal which may be removed by hydrolysis with a suitable acid such as diluted mineral acids such as diluted hydrochloric acid, diluted sulfonic acid; organic sulfonic acid (e.g., p-toluenesulfonic acid, camphor sulfonic acid); polymer supported resins; carboxylic acids (e.g., formic acid, trifluoroacetic acid); $C_{1-3}$ trialkyl silyliodide. This reaction may be carried out in a suitable reaction-inert solvent. Suitable solvents include, for example, aqueous or non-aqueous organic solvents (e.g., tetrahydrofuran, dioxane, acetone, dimethoxyethane, $C_{1-4}$, acetonitrile); halogenated hydrocarbons such as chloroform, dichloroethane. This reaction may be carried out at a temperature of 0° C. to 150° C., preferably from 40° C. to 80° C. for 10 min. to 24 hours, preferably 30 min. to 3 hours.

Thereafter, compound (VI) as obtained above is reacted with compound (VI) in the presence of, or absence of a suitable condensing agent such as Lewis acids, to obtain the 1,4-dihydropyridine compound of the formula (II). This reaction may be carried out in the presence of, or absence of the reaction-inert solvent as listed above. However, this reaction may preferably carried out in the absence of a solvent. This reaction may be carried out at a temperature of 0° C. to 200° C., preferably, from 60° C. to 150° C. for 30 minutes to 48 hours, preferably 10 hours to 20 hours.

In addition, the beta-keto esters (IV) and the substituted benzaldehydes (V) which can be used herein may be either already known or may be prepared by known methods. For example, the beta-keto esters (IV) may be prepared according to the reported methods as shown in, for example, (1) D. Scherling, *J. Labelled Compds. Radiopharm.*, 1989, 27, 599; (2) C. R. Holmquist and E. J. Roskamp, *J. Org. Chem.*, 1989, 54, 3258; (3) S. N. Huckin and L. Weiler, *J. Am. Chem. S C.*, 1974, 96, 1082; (4) *J. C. S. Perkin I*, 1979, 529; and (5)Synthesis, 1986, 37; *J. C. S. Chem. Commun.*, 1977, 932).

Preparation Method B-II:

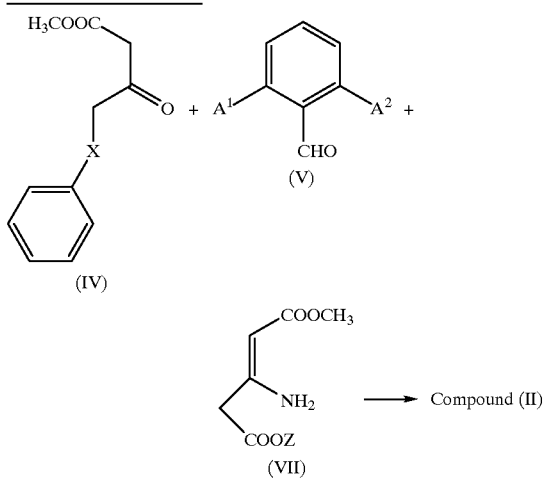

(wherein all the symbols are as already defined, with proviso that X is protected carbonyl, sulfide or sulfoxide)

This method utilizes the three components Hantzsch reaction. In a typical procedure, the beta-keto ester (IV), the substituted benzaldehyde (V) and compound (VI may be heated together in a suitable reaction-inert solvent as listed above (preferably lower alkanols such as methanol and ethanol). Preferably, a small amount of a lower alkanoic acid such as acetic acid is added as catalyst. The reaction mixture may be heated at 0° C. to 200° C., preferably from room temperature to reflux temperature for 30 minutes to 1 week.

Preparation Method B-III:

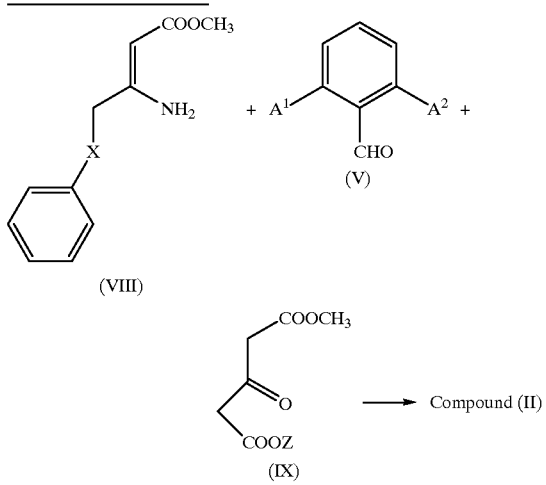

(wherein all the symbols are as already defined, with proviso that X is protected carbonyl, sulfide or sulfoxide)

This method also utilizes the three components Hantzsch reaction as mentioned above. The reaction conditions similar to the above can be also used in this method.

The compound (VIII), enamine may either be known compounds or may be prepared by known methods. For example, the enamine compounds (VIII) may be prepared by reacting the beta-keto ester (IV) with ammonia. More specifically, the beta-keto ester (IV) may be dissolved in a suitable solvent as listed above. Excess amount of ammonia gas is introduced into the solution at a temperature of 0 to 60° C. Alternatively, a solution containing ammonia dissolved in the above solvent is added to the solution containing the beta-keto ester (IV), and the resultant mixture is reacted at a temperature of 0 to 60° C., to obtain compound (VI). In this method, it is easier to modify the moiety -X-phenyl to obtain the dihydropyridine compounds of formula (1) having a desired —CH$_2$-X-phenyl moiety attached to the 6 position of the dihydropyridine (I).

The compounds of formula (1), and the intermediates shown in the above preparation methods can be isolated and purified by conventional procedures, such as recrystallization or chromatographic purification.

As the dihydropyridine compounds of this invention possess at least one asymmetric center, they are capable of occurring in various stereoisomeric forms or configurations. Hence, the compounds can exist in separated (+)- and (−)-optically active forms, as well as in racemic or (+)-mixtures thereof. The present invention includes all such forms within its scope. Individual isomers can be obtained by known methods, such as optically selective reaction or chromatographic separation in the preparation of the final product or its intermediate.

Insofar as the dihydropyridine compounds of this invention are basic compounds, they are capable of forming a wide variety of different salts with various inorganic and organic acids.

The acids which are used to prepare the pharmaceutically acceptable acid addition salts of the aforementioned dihydropyridine base compounds of this invention of formula (I) are those which form non-toxic acid addition salts, i.e., salts containing pharmaceutically acceptable anions, such as the chloride, bromide, iodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1.1'-methylene-bis-(2-hydroxy-3-naphthoate))salts. The acid addition salts can be prepared by conventional procedures.

The dihydropyridine compounds of the present invention of formula (I) exhibit significant bradykinin receptor-binding activity and therefore, are of value in the treatment of a wide variety of clinical conditions in mammals, especially man. Such conditions include inflammation, cardiovascular disease, pain, common cold, allergies, asthma, pancreatitis, burns, virus infection, head injury, multiple trauma and the like.

Therefore, these compounds are readily adapted to therapeutic use as bradykinin antagonists for the control and/or treatment of any of the aforesaid clinical conditions in mammals, including humans.

The activity of the dihydropyridine compounds of the present invention, as bradykinin antagonists, is determined by their ability to inhibit the binding of bradykinin at its receptor sites in IMR90 cells which express B$_2$ receptor employing radioactive ligands.

The bradykinin antagonist activity of the dihydropyridine compounds is evaluated by using the standard assay procedure described in, for example, Baenziger N. L., Jong Y-J. I., Yocum S. A., Dalemar L. R., Wilhelm B., Vaurek R., Stewart J. M., Eur. J. Cell Biol., 1992, 58, 71–80. This method essentially involves determining the concentration of the individual compound required to reduce the amount of radiolabelled bradykinin ligands by 50% at their receptor sites in rat, guinea pig or monkey tissues, or A431 or IMR90 cells, thereby affording characteristic IC$_{50}$ values for each compound tested.

More specifically, the assay is carried out as follows. First, rat, guinea pig or monkey ileum tissues are minced and suspended in 25 mM piperazine-N,N'-bis (2-ethanesulfonic acid (PIPES) buffer (pH 6.8) containing 0.1 mg/ml of soybean trypsin inhibitor. Then, the tissues are homogenized using a Polytron homogenizer at setting #6 for 30 seconds, and centrifuged at 30,000× g for 20 minutes. The pellets are homogenized with the same buffer, and recentrifuged. The tissue pellets, IMR90 cells are suspended in 25 mM PIPES buffer (pH6.8) containing 1.25 mM dithiothreitol, 1.75,ag/ml bacitracin, 125 $\mu$M o-phenanthroline, 6.25 $\mu$M captopril, 1.25 mg/ml bovine serum albumin (BSA), to prepare tissue/cell suspensions. Then, 10 $\mu$l of test compound solution dissolved in phosphate buffered saline (PBS, pH 7.5) containing 2% DMSO (final) and 0.1% BSA (w/v) or 10 $\mu$l of 12.5 $\mu$M bradykinin in PBS (pH 7.5) containing 0.1% BSA (w/v) are placed in a reaction 96-well plate. 15 $\mu$l of 8.3 nM [3H]bradykinin are added to the compound solution or bradykinin solution in the 96-well plate. Finally 100 $\mu$l of the tissue or cell suspension are added to the mixture in the plate, and incubated at 25° C. for 1 hour. After incubation, the resultant product in the reaction plates is filtered through 0.1% polyethylenimine presoaked LKB filermat. The filtrate is washed using a Skatron auto cell harvester. The tissue bound radioactivity is determined using a LKB betaplate counter. The $IC_{50}$ value is determined using the equation:

$$Bound = Bmax/(1+[I]/IC_{50})$$

wherein [I] means the concentration of the test compound.

All compounds prepared in the working examples as described below were tested by this method, and showed an $IC_{50}$ value of 0.2 nM to 10 nM with respect to inhibition of binding at its receptor.

The bradykinin antagonist activity of the dihydropyridine compounds in vivo is evaluated by a plasma leakage test. This test essentially involve determining the concentration of the individual compound required to reduce by 50% the amount of bradykinin-induced plasma leakage in rat urinary bladder, thereby affording characteristic $ED_{50}$ values for each compounds tested.

More specifically, the assay is carried out as follows. 3.5-week old male Sprague-Dawlew rats are purchased from Charles River Japan Inc. The rats are fed on stock diet (CRF from Charles River Japan, Inc.) and maintained under the standard conditions (temperature, 23±1° C. and humidity 55±5%) for at least 3 days. The rats are fasted overnight prior to the experiments. Each test group consists of 5 rats.

Bradykinin, purchased from Peptide Ins., is dissolved in the physiological saline (0.9% sodium chloride) at a concentration of 10 nmol/ml. The test dihydropyridine compounds are dissolved or suspended at different concentrations in the physiological saline solution containing 10 mg/ml Evans blue (Wako Pure Chemical, Japan).

Captopril (5 mg/kg of body weight) is intraperitoneally (i.p.) injected to the rats, and 20 min later the rats are anesthetized by an administration of Nembutal (Abbott) (2.5 mg/kg of body weight). 5 min later, the test compound solution containing Evans blue is intravenously (i.v.) injected to the rats at a dose of 3 ml/kg of body weight. Another 5 min later, bradykinin is i.v. injected at a dose of 10 nmol/kg body weight. Thereafter, the rats are killed by dislocation of the neck and the urinary bladders are obtained. The urinary bladders are individually treated with 1 ml of formamide at 60° C. for at least 16 hours to extract Evans blue from the tissue. The absorbance of the extract is measured spectrophotometrically at 605 nm to determined the dye concentration. The effect of the individual test compound is calculated as a percentage of the amount of Evans blue leaked into the urinary bladder as compared to the control (saline for the test compounds). Some compounds prepared in the working examples as described below exhibited a remarkable activity at a concentration of 0.2 $\mu$M in the inhibition of urinary bladder leakage in this test system, whereas some structurally similar compounds (such as dimethyl 4-(2,6-dichlorophenyl)-6-[2-(2-methoxyphenyl)ethyl]-2-[4-(8-methyl-8-azabicyclo[3.2.1]oct-3-yl)-1-piperazinyl]carbonylmethyl-1,4-dihydropyridine-3,5-dicarboxylate) did not show significant in vivo activity at a concentration of 1.5 $\mu$M.

The dihydropyridine compounds of formula (I) of this invention can be administered via either the oral, parenteral or topical routes to mammals. In general, these compounds are most desirably administered to humans in doses ranging from 0.3 mg to 750 mg per day, preferably from 10 mg to 500 mg per day, although variations will necessarily occur depending upon the weight and condition of the subject being treated, the disease state being treated and the particular route of administration chosen. However, for example, a dosage level that is in the range of from 0.06 mg to 2 mg per kg of body weight per day is most desirably employed for the treatment of inflammation.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral-pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as filuers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES

The present invention is illustrated by the following examples. However, it should be understood that the invention is not limited to the specific details of these examples. Melting points were taken with a Buchi micro melting point apparatus and uncorrected. Infrared Ray absorption spectra (IR) were measured by a Shimazu infrared spectrometer (IR-470). $^1$H and $^{13}$C nuclear magnetic resonance spectra (NMR) were measured in $CDCl_3$ by a JEOL NMR spectrometer (JNM-GX270, 270 MHz) unless otherwise indicated and peak positions are expressed in parts per million (ppm) downfield from tetramethylsilane or from t-butanol (1.28 ppm in $D_2O$). The peak shapes are denoted as follows: s, singlet; d, doublet; t, triplet; m, multiplet; br, broad.

Example 1

Dimethyl 4-(2,6-dichlorophenyl)-2-[4-(8-methyl-8-azabicyclo[3.2.1]oct-3-yl)-1-piperazinyl]carbonylmethyl-6-phenylsulfinylmethyl-1,4-dihydropyridine-3,5-dicarboxylate dihydrochloride A. Methyl 2-(2,6-Dichlorophenylmethylidene)-3-oxo-4-phenylthiobutanoate Sodium hydride (17.32 g, 0.433 mol) was washed with hexane (100 ml×2) then was suspended in dimethylformamide (300 ml). To the mixture was dropwise added thiophenol (44.5 ml, 0.433 mol) in DMF (50 ml) under ice-methanol bath cooling with controlling the inner temperature of 5–10° C. under nitrogen atmosphere. After 1.5 h stirring at −5° C., methyl 4-chloroacetoacetate (50 ml, 0.433 mol) was dropwise added to the reaction mixture under ice-methanol bath cooling with controlling the inner temperature of 5–10° C. under nitrogen atmosphere and the reaction mixture was stirred at room temperature overnight. The mixture was acidified with 1N HCl to pH 2 under ice bath cooling then partitioned between EtOAc (500 ml) and $H_2O$ (100 ml). The aqueous phase was extracted with EtOAc (250 ml×2). The combined extracts were concentrated to about 500 ml and then washed with aq. $NaHCO_3$ solution (150 ml) and brine (100 ml×3). The organic solution was dried over $MgSO_4$ and concentrated to afford 100.88 g of methyl 4-phenylthioacetoacetate as an orange color oil. (104% yield).(contained ⅙ eq of DMF) $^1$H NMR ($CDCl_3$) 7.42–7.18 (m, 5H), 3.80 (s 2H), 3.71 (s, 3H), 3.65 (s, 2H).

To this oil was added 2,6-dichlorobenzaldehyde (75.9 g, 0.433 mol), acetic acid (5.5 ml g, 96 mmol), piperidine (5.5 ml, 55.6 mmol) and benzene (300 ml). This mixture was distilled for removal of the initial distillate (about 50 ml) then replaced the distillation apparatus to Dean Stark trap and refluxed with azeotropic removal of water for 2 h. The mixture was diluted with EtOAc (500 ml) and washed with 1N HCl (100 ml), sat. $NaHCO_3$ (100 ml) and then brine (100 ml×3) The organic solution was dried over $MgSO_4$ and concentrated in vacuo to give a yellow oil which was purified by column chromatography on silica gel (2 Kg, hexane/ethyl acetate: 50/1, 10/1, then 5/1 as eluent) to give 136.63 g (82.8%) of a benzylidene derivative. This is a 3:1 mixture of the double bond isomers.

$^1$H NMR ($CDCl_3$) 7.72 (s, 0.25H), 7.66 (s, 0.75H), 7.17–7.40 (m, 8H), 4.12 (s, 1.5H), 4.02 (s, 0.5H), 3.82 (s, 0.75H), 3.64 (s, 2.25H).

B. Dimethyl 4-(2 6-dichlorophenyl)-2-methoxycarbonylmethyl-6-phenylthiomethyl-1,4-dihydropyridine-3,5-dicarboxylate A mixture of methyl 2-(2,6-dichlorophenylmethylidene)-3-oxo-4-phenylthiobutanoate (14.21 g, 39.9 mmol) and dimethyl 3-aminoglutaconate (6.44 g, 37.2 mmol) was heated at 120° C. for 13 h. After cooling down to room temperature, the reaction mixture was purified by column chromatography on silica gel (hexane/ethyl acetate: 4/1 as eluent) to afford 8.10 g (40.6%) of a wine red color viscous oil.

$^1$H NMR ($CDCl_3$) δ 7.69 (br. s, 1H), 7.41–7.21 (m, 7H), 6.99 (dd, J=7.7, 8.4 Hz, 1H), 5.98 (s, 1H), 4.52 (d, J=16.5 Hz, 1H), 4.23 (d, J=16.5 Hz, 1H), 3.86 (d, J=16.5 Hz, 1H), 3.66 (s, 3H), 3.61 (d, J=16.5 Hz, 1H), 3.53 (s, 3H), 3.52 (s, 3H), IR (neat): 3350, 1740, 1700, 1650, 1625 cm$^{-1}$.

C. Dimethyl 4-(2,6-dichlorophenyl)-2-methoxycarbonylmethyl-6-phenylsulfinylmethyl-1,4-dihydropyridine-3,5-dicarboxylate To a stirred solution of dimethyl 4-(2,6-dichlorophenyl)-2-methoxycarbonylmethyl-6-phenylthiomethyl-1,4-dihydropyridine-3,5-dicarboxylate (6.37 g, 11.9 m mol) in $CH_2Cl_2$ (300 ml) was added 3-chloroperoxybenzoic acid (70%, 2.9 g, 11.9 mmol) at 0° C. After 1 h stirring at 0° C., the reaction mixture was washed with saturated aqueous $K_2CO_3$ solution, water and brine. After the solution was dried over $MgSO_4$, the solvent was evaporated to give 2.64 g of a yellow amorphous solid, which was purified by column chromatography on silica gel (600 g, methanol/$CH_2Cl_2$: 1/60 to 1/40 as eluent) to provide 1.8 g of the desired product as diastereomeric mixture. Recrystallization of the product from ethyl acetate/isopropyl ether gave more polar rich diastereomeric mixture of which ratio was identified by a TLC developed by $CH_2Cl_2$ methanol (20:1, three times development). The second crop from the mother liquid gave 1:1 mixture of the diastereomers. Third crop from the resulting mother liquid gave a pure less polar isomer 542 mg as a white powder, mp 109.0–109.2° C.

$^1$H NMR ($CDCl_3$) δ 7.73–7.67(m, 3H), 7.60–7.52 (m, 3H), 7.26 (d, J=8.1 Hz, 2H), 7.04 (t, J=8.1 Hz, 1H), 5.90(s, 1H), 4.57 (d, J=13.6 Hz, 1H), 4.05 (d, J=13.6 Hz, 1H), 3.94 (d, J=16.8 Hz, 1E), 3.75 (s, 3H), 3.52 (s, 3H), 3.50 (d, J=16.8 Hz, 1H), 3.48 (s, 3H).

D. Dimethyl 4-(2 6-dichlorophenyl)-2-[4-(8-methyl-8-azabicyclo[3.2.1]oct-3-yl)-1-piperazinyl]carbonylmethyl-6-phenylsulfinylmethyl-1,4-dihydropyridine-3,5-dicarboxylate To a suspension of the above triester (542 mg, 0.98 m mol) in 1,4-dioxane was added 2N NaOH. The color of the mixture turned to red. The mixture was stirred for 20 min. To the mixture was added 20% $NaH_2PO_4$ solution (20 ml) and 2N HCl (4 ml) to pH 3. Then the whole was extracted with $CH_2Cl_2$ (30 ml×2). The combined extracts were washed with brine (10 ml), dried ($MgSO_4$) and concentrated in vacuo to give a yellow amorphus solid (620 mg).

$^1$H NMR ($CDCl_3$) δ 8.37 (br.s, 1H), 7.80–7.74 (m, 2H), 7.57–7.49 (m, 3H), 7.27 (d, J=8.1 Hz, 2H), 7.03 (t, J-7.9 Hz, 1H), 6.02 (s, 1H), 4.74 (d, J=12.8 Hz, 1H), 3.98 (d, J=16.1 Hz, 1H), 3.91 (d, J=12.8 Hz, 1M), 3.73 (d, J=16.1 Hz, 1H), 3.59 (s, 3H), 3.53 (s, 3H)

The acid (620 mg) was dissolved in dry $CH_2Cl_2$ (10 ml) to give white precipitation. Then N-i-ethyl-3-(3-dimethylaminopropyl)carbodiimide hydrochloride (249 mg, 1.3 mmol) was added and stirred at 0° C. under nitrogen atmosphere for 30 min. To the clear yellow solution was added 1-(8-methyl-8-azabicyclo[3.2.1]oct-3-yl)piperazine and stirred at ambient temperature overnight. The whole was partitioned between water (10 ml) and $CH_2Cl_2$ (40 ml) to form a heavy emulsion, thus sat $NaHCO_3$ solution (10 ml) was added and extracted with $CH_2Cl_2$ (30 ml×3). The combined extracts were dried over $MgSO_4$ and concentrated in vacuo to give a yellow oil. Chromatography on silica gel(25 g) eluted with $CH_2Cl_2$-methanol-triethylamine (4:1:0.025) gave a yellow oil (450 mg).

$^1$H NMR ($CDCl_3$) δ 8.36 (br.s, 1H), 7.80–7.73 (m, 2H), 7.57–7.46 (m, 3H), 7.26 (d, J=8.1 Hz, 2H), 7.02 (t, J=8.4 Hz, 1H), 5.98 (s, 1H), 4.55 (d, J=12.8 Hz, 1H), 3.99 (d, J=15.3 Hz, 1H), 3.85 (d, J=13.4 Hz, 1H), 3.78 (d, J=15.3 Hz, 1H), 3.53 (s, 3H), 3.52, (s, 3H), 3.69–3.48 (m, 4H), 3.30–3.10 (m, 4H), 2.63–1.45 (m, 14H).

This product was dissolved in methanol (5 ml) and 5% HCl in methanol (2 ml) was added. The mixture was concentrated in vacuo to give a yellow amorphus solid. Crystallization from isopropanol gave a yellow solid (254 mg, 30% yield).

mp 203.0–204.2 (dec.)

hu 1H NMR ($D_2O$) δ 7.77–7.69 (m 2H), 7.39–7.30 (m 21), 7.16–7.04 (m, 11), 5.84 (s, 1H), 4,38–3.00 (m, 21H), 2.85 (s, 3H), 2.02–2.55 (m, 8H).

IR (KBr): 1691, 1652, 1628

Example 2

Dimethyl 4-(2,6-dichlorophenyl)-2-[4-(8-methyl-8-azabicyclo[3.2.1]oct-3-yl)-1-piperazinyl]carbonylmethyl-6-(2-oxo-2-phenylethyl)-1,4-dihydropyridine- 3,5-dicarboxylate dihydrochloride A. Methyl 5-(1.3-dioxolan-2-yl)-3-oxo-5-phenylpentanoate To a stirred solution of 3-(1,3-dioxolan-2-yl)-3-phenylpropionic acid (prepared according to Yamaguchi's procedure: *J. Chem. Soc. Chem. Commun.*, 1988, 27; 23.68 g, 114 mmol) and Meldrum's acid (13.69 g, 95 mmol) in THF (200 ml) was added diethyl phosphorocyanidate (18.3 ml, 114 mmol) and trietylamine (40 ml, 287 mmol) dropwise at 0° C. The reaction mixture was stirred at 0° C. for 2 h and at ambient temperature for 16 h. The solvent was evaporated and 5% $NaHCO_3$ aqueous solution was added to the residue. The aqueous solution was washed with ethyl acetate. The aqueous layer was then acidified with c-HCl and extracted with ethyl acetate. The combined extracts were washed with brine and dried ($MgSO_4$). Evaporation of the solvent afforded 14.05 g of a brown color oil solid mixture which was washed with methanol to give 5.92 g of a white solid. The organic layer was dried ($MgSO_4$) and concentrated to give 34.40 g of a brown viscous oil. Methanol was added to this oil to form solid, which was collected by filtration and washed with methanol to afford 5.51 g of a pale yellow solid. Total 11.43 g (36%) of Meldrum's acid derivative was obtained. This was refluxed in methanol (40 ml) for 4 h. The solvent was evaporated to give a yellow viscous oil which was purified by column chromatography on silica gel (hexane/ethyl acetate: 4/1 as eluent) to afford 7.69 g (85.1%) of the title compound as a pale yellow clear oil.

$^1$H NMR ($CDCl_3$) δ 11.96 (br. s, 0.1H), 7.49–7.46 (m, 2.2H), 7.39–7.31 (m, 3.3H), 5.02 (s, 0.1H), 4.09–4.00 (m, 2.2H), 3.86–3.76 (m, 2.2H), 3.72 (s, 3H), 3.70 (s, 0.3H), 3.58 (s, 2H), 3.13 (s, 2H), 2.82 (s, 0.2H). 3659, 3550, 1740, 1715, 1650, 1630 cm$^{-1}$. Anal. Calcd for $C_{14}H_{16}O_5$: C, 63.62; H, 6.10. Found: C, 63.17; H, 6.16.

B. Dimethyl 4-(2,6-dichlorophenyl)-6-[2-(1,3-dioxolan-2-yl)-2-phenylethyl]-2-methoxycarbonylmethyl-1,4-dihydropyridine-3,5-dicarboxylate This was prepared by a procedure similar to that described in Example 1-B, as a pale yellow solid, mp 56–57° C.

$^1$H NMR ($CDCl_3$) δ 7.62 (br. s, 1H), 7.51 (dd, J=1.8, 8.1 Hz, 2H), 7.38–7.27 (m, 3H), 7.22 (d, J=8.1 Hz, 2H), 6.97 (dd, J=7.3, 8.1 Hz, 1H), 5.98 (s, 1H), 4.17–4.08 (m, 2H), 3.87–3.70 (m, 2H), 3.85 (d, J=15.8 Hz, 1H), 3.76 (d, J=14.8 Hz, 1H), 3.76 (s, 3H), 3.68 (d, J=16.5 Hz, 1H), 3.52.(s, 3H), 3.49 (s, 3H), 3.30 (d, J=15.4 Hz, 1H).

IR (nujol): 3340, 1745, 1700, 1660, 1650, 1630cm$^{-1}$.

C. Dimethyl 4-(2,6-dichlorophenyl)-2-[4-(8-methyl-8-azabicyclo[3.2.1]oct-3-yl)-1-piperazinyl]carbonylmethyl-6-(2-oxo-2-phenylethyl)-1,4-dihydropyridine-3,5-dicarboxylate A mixture of the above triester derivative (2.07 g, 3.59 mmol), 2N NaOH aqueous solution (3.6 ml, 7.18 mmol), and 1,4-dioxane (7.0 ml) was stirred at room temperature for 0.5 h. To the mixture was added aqueous 20% $NaH_2PO_4$ solution (30 ml), and 1N HCl (7.5 ml). The whole was extracted with $CH_2Cl_2$ (60 ml×2) and the combined extracts were washed brine (20 ml). The solution was dried over $MgSO_4$ and concentrated in vacuo to give a yellow amorphus solid (3.73 g).

$^1$H NMR ($CDCl_3$) δ 8.22 (br.s, 1H), 7.47–7.40 (m, 2H), 7.30–7.12 (m, 5H), 6.89 (t, J=8.1, 1H), 5.91 (s, 1H), 4.10–3.95 (m, 2H), 3.80–3.00 (m, 12H).

To a stirred solution of the crude acid (3.73 g) in $CH_2Cl_2$ (12 ml) was added N-1-ethyl-3-(3-dimethyl-aminopropyl) carbodiimide hydrochloride (0.29 g, 1.5 mmol) at 0° C. and stirred at 0° C. for 30 min under nitrogen atmosphere. To the mixture was added 1-(8-methyl-8-azabicyclo[3.2.1]oct-3-yl)piperazine and stirred at ambient temperature for 15 min while most of the amine was not dissolved, thus dimethyl formamide (6 ml) was added. The mixture was turned to mostly clear solution then yellow turbid mixture. The mixture was stirred at 0° C. to ambient temperature under nitrogen atmosphere overnight. To the mixture was added $H_2O$ (15 ml), $CH_2Cl_2$ (70 ml) and hexane (20 ml). The aqueous layer was extracted with $CH_2Cl_2$-hexane (3:1 mixture, 30 ml). The combined extract was dried over $MgSO_4$ and concentrated in vacuo to give a yellow oil. Chromatography on silica gel eluted with $CH_2Cl_2$-methanol (10:1) then $CH_2Cl_2$-methanol-triethylamine (4:1:0.05) gave a light yellow amorphus solid (1.80 g) Crystallization from isopropyl ether-ethyl acetate gave a pale yellow solid (1.47 g, 54.4%).

$^1$H NMR ($CDCl_3$) 6 8.44 (br.s, 1H), 7.56–7.50 (m, 2H), 7.38–7.19 (m, 5H), 6.98 (t, J=7.9 Hz, 1H), 5.99 (s, 1H), 4.48 (d, J=14.3 Hz, 1H), 4.17–4.07 (m, 2H), 3.86–3.72 (m, 2H), 3.68–3.52 (m, 7H), 3.53 (s, 3H), 3.49 (s, 3H), 3.38 (d, 15.4 Hz, 1H), 3.25 (br. s, 2H), 2.69–2.45 (m, 4H), 2.31 (s, 3H), 2.07–1.98 (m, 2H), 1.83–1.52 (m, 6H)

A suspension of the acetal (1.47 g, 1.95 m mol) in acetone (50 ml) was added 2N HCl and stirred at 60° C. for 2.5 hr. The whole was concentrated in vacuo and the water in the mixture was azeotropically removed with ethanol and isopropanol. The residue was recrystallized from isopropanol to give a pale yellow solid which was dried at 80° C. for 12 hrs and the 100° C. for 10 hr (890 mg).

mp 209.5–210.5° C. (dec.)

$^1$H NMR ($D_2O$) δ 7.96 (br. d, J=7.7 Hz, 21, 7.72–7.60 (m, 1H), 7.58–7.47 (m, 2H), 7.32 (d, J=7.7 Hz, 2H), 7.11–7.00 (m, 1H), 5.96 (s, 1H), 4.60–4.48 (m, 1H), 4.30–3.10 (m, 20H), 2.84 (s, 3H), 2.52–2.00 (m, 8H).

IR (KBr): 1693, 1654, 1630

Example 3

Dimethyl 4-(2,6-dichlorophenyl)-(2-oxo-2-phenylethyl)-2-[4-(3-quinuclidinyl)-1-piperazinyl]carbonylmethyl-1,4-dihydropyridine-3,5-dicarboxylate dihydrochloride This was prepared by a procedure similar to that described in Example 2-C, as a yellow solid.

mp :201.0–202.4° C.
¹H-NMR (DMSO-d₆): δ 8.07–7.96 (m, 2H), 7.72–7.45 (m, 4H), 7.35 (d, J=7.5 Hz, 2H), 7.15 (dd, J=7.5, 8.4 Hz, 1H), 5.90 (s, 1H), 4.63–4.48 (m, 1H), 4.26–4.12 (m, 2H), 3.90–2.88 (m, 22H), 2.55–1.60 (m, 5H).
IR (KBr): 1695, 1653, 1645, 1636, 1624 cm⁻¹.

Example 4

Dimethyl 4-(2,6-dichlorophenyl)-(2-oxo-2-phenylethyl)-2-[4-(3-hydroxy-bicyclo[3.3.0]oct-7-yl)piperazin-1-yl]carbonylmethyl-1,4-dihydropyridine-3,5-dicarboxylate hydrochloride This was prepared by a procedure similar to that described in Example 2-C, as a yellow solid.
mp: 164.0–166.0° C.
¹H-NMR (DMSO-d₆): δ 8.06–7.97 (m, 2H), 7.71–7.48 (m, 4H), 7.35 (d, J=8.0 Hz, 2H), 7.15 (t, J=8.0 Hz, 1H,), 5.90 (s, 1H), 4.70–4.02 (m, 8H), 3.68–2.80 (m, 6H), 3.40 (s, 3H), 3.27 (s, 3H), 2.42–2.18 (m, 4H), 1.95–1.31 (m, 6H).
IR (KBr): 3450, 1694, 1652, 1645, 1625 cm⁻¹.

Example 5

Dimethyl 4-(2,6-dichlorophenyl)-2-{2-[1-(hydroxy)cyclopentyl]ethylpiperazinyl}carbonylmethyl-6-phenylsulfinylmethyl-1,4-dihydropyridine-3,5-dicarboxylate This was prepared by a procedure similar to that described in Example 1-D, as a white solid.
mp : 216–216.5° C. (decomposed)
¹H-NMR (CDCl₃): s 8.04 (br s, 1H), 7.77–7.72 (m, 2H), 7.58–7.48 (m, 3H), 7.27 (d, J=8.1 Hz, 2H), 7.02 (t, J=7.9 Hz, 1H), 5.99 (s, 1H), 4.51 (d, J=12.8 Hz, 1H), 3.93–3.84 (m, 3H), 3.72–3.55 (m, 4H), 3.53 (s, 3H), 3.52 (s, 3H), 2.70–2.63 (m, 2H), 2.56–2.48 (m, 6H), 1.89–1.43 (m, 10H).
IR (KBr): 1699, 1684, 1661, 1620, 1513, 1446, 1432, 1288, 1219, 1193, 1158, 1101, 1028, 1019 cm⁻¹.

Example 6

Dimethyl 4-(2,6-dichlorophenyl)-2-[4-(8-methyl-8-azabicyclo[3,2,1]octan-3-yl)-1-piperazinyl]carbonylmethyl-6-(phenylsulfonylmethyl-1,4-dihydropyridine-3,5-dicarboxylate dihydrochloride This was prepared by a procedure similar to that described in Example 1-D, as a yellow solid.
mp: 196.0–199.0° C. (decomposed)
1H-NMR (DMSO, HCl salt): δ 10.8 (br s, 1H), 9.20 (br s, 1H), 7.92–7.85 (m, 2H), 7.80–7.70 (m, 1H), 7.65–7.57 (m, 1H), 7.29–7.36 (m, 2H), 7.20–7.11 (m, 1H), 5.89 (s, 1H), 5.20–5.17 (m, 1H), 4.60–1.90 (m).
IR (KBr): 1690, 1515, 1446, 1438, 1290 cm⁻¹.

Example 7

Dimethyl 4-(2,6-dichlorophenyl)-2-[4-(3-hydroxy-bicyclo[3,3,0]oct-7-yl)-1-piperazinyl]carbonylmethyl-6-(phenylsulfinylmethyl-1,4-dihydropyridine-3,5-dicarboxylate monohydrochloride This was prepared by a procedure similar to that described in Example 1-D, as a yellow solid.
free base:
¹H-NMR (CDCl₃): δ 8.20 (br s,1H), 7.78–7.73 (m, 2H), 7.57–7.48 (m, 3H), 7.26 (d, J=8.1 Hz, 2H), 7.02 (t, J=1.1Hz, 1H), 5.97 (s, 1H), 4.53 (d, J=12.5 Hz, 1H), 3.97 (d, J=15.4 Hz, 1H), 3.86 (d, J=12.8 Hz, 1H), 3.80 (d, J=15.4 Hz, 1H), 3.70–3.55 (m, 4H), 3.53 (s, 6H), 2.62–2.34 (m, 9H), 2.18–2.00 (m, 4H), 1.60–1.42 (m, 2H).
HCl salt:
mp: 198.0–200.0° C. (decomposed)
¹H-NMR (DMSO): δ 11.0 (br s, 1H), 9.55–9.30 (m, 1H), 7.80–7.73 (m, 2H), 7.68–7.55 (m, 3H), 7.38 (d, J=7.7 Hz, 2H), 7.19 (t, J=7.9 Hz, 1H), 5.93 (s, 1H), 4.80–1.30 (m).
IR (KBr): 3,400, 2950, 1690, 1670, 1652, 1647, 1638, 1512, 1435, 1290, 1192, 1101 cm⁻¹.

Example 8

Dimethyl 4-(2.6-dichlorophenyl)-2-(4-cycloheptyl-piperazinyl)carbonylmethyl-6-phenylsulfinylmethyl-1,4-dihydropyridine-3,5 -dicarboxylate, monohydrochloride This was prepared by a procedure similar to that described in Example 1-D, as a yellow solid.
free base:
¹H-NMR (CDCl₃): s 8.20 (bv, 1H), 7.80–7.70 (m, 2H), 7.58–7.45 (m, 3H), 7.26 (d, J=8.1 Hz, 2H), 7.02 (dd, J=7.8, 8.4 Hz, 1H), 5.98 (s, 1H), 4.49 (d, J=12.6 Hz, 1H), 3.91 (d, J=12.6 Hz, 1H), 3.89 (s, 2H), 3.75–3.44 (m, 4H), 3.54 (s, 3H), 3.53 (s, 3H), 2.62–2.42 (m, 5H), 2.00–1.30 (m, 12H).
HCl salt:
mp: 226.0–228.0° C. (decomposed)
¹H-NMR (DMSO-d6, HCl salt): δ 9.41 (bv, 1H), 7.81–7.52 (m, 5H), 7.38 (d, J=8.1 Hz, 2H), 7.19 (dd, J=7.8, 8.4 Hz, 1H), 5.93 (s, 1H), 4.54–2.68 (m, 13H), 3.47 (s, 3H), 3.40 (s, 3H), 2.20–1.98 (m, 2H), 1.79–1.30 (m, 10H).
IR (KBr): 3430, 2945, 1688, 1656, 1622 cm⁻¹.

Example 9

Dimethyl 4-(2,6-dichlorophenyl)-2-(4-cyclohexyl-piperazinyl)carbonylmethyl-6-phenyslulfinylmethyl-1,4-dihydropyridine-3,5-dicarboxylate, monohydrochloride This was prepared by a procedure similar to that described in Example 1-D, as a yellow solid.
free base:
¹H-NMR (CDCl₃): δ 8.25 (bv, 1H), 7.80–7.72 (m, 2H), 7.59–7.47 (m, 3H), 7.26 (d, J=7.8 Hz, 2H), 7.01 (t, J=7.8 Hz, 1H), 5.98 (s, 1H), 4.51 (d, J=12.6 Hz, 1H), 3.95 (d, J=15.6 Hz, 1H), 3.89 (d, J=12.6 Hz, 1H), 3.84 (d, J=15.6 Hz, 1H), 3.73–3.47 (m, 4H), 3.53 (s, 6H), 2.61–2.47 (m, 5H), 1.88–1.02 (m, 10H).
HCl salt:
mp: 215.0–217.2° C. (decomposed)
¹H-NMR (DMSO-d6, HCl salt): δ 10.86–10.56 (m, 1H), 9.39 (bv, 1H), 7.82– 7.53 (m, 5H), 7.38 (d, J=8.1 Hz, 2H), 7.19 (dd, J=7.8, 8.4 Hz, 1H), 5.93 (s, 1H), 4.53–4.07 (m, 4H), 3.97–2.66 (m, 9H), 3.46 (s, 3H), 3.40 (s, 3H), 2.18–1.00 (m, 10H).
IR (KBr): 3430, 2950, 1690, 1660, 1622 cm⁻¹.

Example 10

Dimethyl 4-(2,6-dichlorophenyl)-2-(4-cyclooctyl-piperazinyl)carbonylmethyl-6-phenylsulfinylmethyl-1,4-dihydropyridine-3,5-dicarboxylate, monohydrochloride This was prepared by a procedure similar to that described in Example 1-D, as a yellow solid.
free base:
¹H-NMR (CDCl₃): δ 8.17 (bv, 1H), 7.81–7.72 (m, 2H), 7.60–7.47 (m, 3H), 7.26 (d, J=8.1 Hz, 2H), 7.02 (t, J=8.1 Hz, 1H), 5.98 (s, 1H), 4.49 (d, J=12.6 Hz, 1H), 3.91 (d, J=12.6 Hz, 1H), 3.89 (s, 2H), 3.75–3.46 (m, 4H), 3.54 (s,3H), 3.53 (s, 3H), 2.67–2.43 (m, 5H), 1.80–1.35 (m, 14H).
HCl salt:
mp: 242.2–242.9° C. (decomposed)
¹H-NMR (DMSO-d₆): δ 10.72–10.43 (m, 1H), 9.42 (bv, 1H), 7.81–7.52 (m, 5H), 7.38 (d, J=8.0 Hz, 2H), 7.20 (t, J=8.0 Hz, 1H), 5.93 (s, 1H), 4.52–2.72 (m, 13H), 3.47 (s, 3H), 3.40 (s, 3H), 2.10–1.31 (m, 14H).
IR (KBr): 3440, 2930, 1687, 1654, 1621 cm⁻¹.

Example 11

Dimethyl 4-(2,6-dichlorophenyl)-2-[4-(3-oxo-bicyclo[3,3,0]oct-7 yl) piperazinyl]-carbonylmethyl-6- phenylsulfinylmethyl-1,4-dihydropyridine-3,5-dicarboxylate, monocitric acid

This was prepared by a procedure similar to that described in Example 1-D, as a yellow solid.

free base:
$^1$H-NMR (CDCl$_3$): δ 8.12 (bv, 1H), 7.82–7.71 (m, 2H), 7.60–7.47 (m, 3H), 7.27 (d, J=8.1 Hz, 2H), 7.02 (dd, J=7.8, 8.4 Hz, 1H), 5.98 (s, 1H), 4.51 (d, J=12.6 Hz, 1H), 3.98–3.82 (m, 3H), 3.75–3.52 (m, 4H), 3.54 (s, 3H), 3.53 (s, 3H), 2.79–2.40 (m, 9H), 2.30–2.04 (m, 4H), 1.43–1.22 (m, 2H).

citrate:
mp: 132.5–134.0° C.
$^1$H-NMR (DMSO-d$_6$): 6 9.26 (bv, 1H), 7.80–7.53 (m, 5H), 7.37 (d, J=8.1 Hz, 2H), 7.18 (dd, J=7.8, 8.4 Hz, 1H), 5.92 (s, 1H), 4.41 (d, J=12.6 Hz, 1H), 3.99 (d, J=15.6 Hz, 1H), 3.70 (d, J=12.6 Hz, 1H), 3.46 (s, 3H), 3.39 (s, 3H), 3.60–1.91 (m, 22H), 1.46–1.23 (m, 2H).
IR (KBr): 3425, 2950, 1730, 1691, 1637, 1624 cm$^{-1}$.

Example 12

Dimethyl 4-(2,6-dichlorophenyl)-2-[4-(cis-1,5-dimethyl-3-oxo-bicyclo[3,3,0]oct-7-yl)-piperazinyl]carbonylmethyl-6-phenylsulfinylmethyl-1,4-dihydropyridine-3,5-dicarboxylate, monohydrochloride This was prepared by a procedure similar to that described in Example 1-D, as a yellow solid.

free base:
$^1$H-NMR (CDCl$_3$): δ 8.13 (bv, 1H), 7.81–7.70 (m, 2H), 7.59–7.47 (m, 3H), 7.27 (d, J=8.0 Hz, 2H), 7.02 (t, J=8.0 Hz, 1H), 5.98 (s, 1H), 4.52 (d, J=12.6 Hz, 1H), 3.98–3.80 (m, 3H), 3.72–3.45 (m, 4H), 3.54 (s, 3H), 3.53 (s, 3H), 2.52–2.10 (m, 9H), 1.98–1.62 (m, 4H), 1.13 (s, 1.5H), 1.06 (s, 4.5H).

HCl salt:
mp: 192.0–194.6° C.
$^1$H-NMR (DMSO-d$_6$): δ 9.41–9.26 (m, 1H), 7.82–7.53 (m, 5H), 7.38 (d, J=8.1 Hz, 2H), 7.19 (dd, J=7.8, 8.4 Hz, 1H), 5.93 (s, 1H), 4.50–4.08 (m, 4H), 3.95–1.92 (m, 23H), 1.02 (s, 1.5H), 1.01 (s, 4.5H).
IR (KBr): 3445, 2955, 1732, 1691, 1646, 1638 cm$^{-1}$.

Example 13

Dimethyl 4-(2,6-dichlorophenyl)-2-[4-(5-oxo-cyclooctyl)-piperazinyl]carbonylmethyl-6-phenylsulfinylmethyl-1,4-dihydropyridine-3,5-dicarboxylate, monohydrochloride This was prepared by a procedure similar to that described in Example 1-D, as a yellow solid.

free base:
$^1$H-NMR (CDCl$_3$): δ 8.16–8.06 (m, 1H), 7.80–7.71 (m, 2H), 7.60–7.47 (m, 3H), 7.26 (d, J=8.1 Hz, 2H), 7.02 (t, J=8.1 Hz, 1H), 5.98 (s, 1H), 4.50 (d, J=12.6 Hz, 1H), 3.98–3.78 (m, 3H), 3.78–3.45 (m, 4H), 3.54 (s, 3H), 3.53 (s, 3H), 2.64–1.38 (m, 17H).

HCl salt:
mp: 232.5–234.0° C. (decomposed)
$^1$H-NMR (DMSO-d6, HCl salt): δ 10.69–10.39 (m, 1H), 9.38 (s, 1H), 7.81–7.52 (m, 5H), 7.38 (d, J=8.1 Hz, 2H), 7.19 (t, J=8.1 Hz, 1H), 5.92 (s, 1H), 3.46 (s, 3H), 3.40 (s, 3H), 4.52–1.50 (m, 25H).
IR (KBr): 3435, 2950, 1692, 1651, 1646, 1625 cm$^{-1}$.

Example 14

Dimethyl 4-(2,6-dichlorophenyl)-2-[4-(1,4-dioxaspiro[4,5]dec-8-yl)piperazinyl]-carbonylmethyl-6-phenylsulfinylmethyl-1,4-dihydropyridine-3,5-dicarboxylate This was prepared by a procedure similar to that described in Example 1-D, as a yellow solid.

mp: 117.0–119.0° C.
$^1$H-NMR (CDCl$_3$): 6 8.16 (bv, 1H), 7.82–7.71 (m, 2H), 7.60–7.48 (m, 3H), 7.26 (d, J=8.1 Hz, 2H), 7.02 (dd, J=7.8, 8.4 Hz, 1H), 5.98 (s, 1H), 4.51 (d, J=12.6 Hz, 1H), 3.93 (s, 4H), 3.94–3.83 (m, 3H), 3.77–3.42 (m, 4H), 3.54 (s, 3H), 3.53 (s, 3H), 2.73–2.31 (m, 5H) 1.90–1.43 (m, 8H).
IR (KBr): 3450, 1696, 1691, 1645, 1625 cm$^{-1}$.

Example 15

Dimethyl 4-(2,6-dichlorophenyl)-2-[4-(4-oxo-cyclohexyl)-piperazinyl]carbonylmethyl-6-phenylsulfinylmethyl-1,4-dihydropyridine-3,5-dicarboxylate, monohydrochloride This was prepared by a procedure similar to that described in Example 1-D, as a yellow solid. free base:
$^1$H-NMR (CDCl$_3$): δ 8.16 (bv, 1H), 7.81–7.70 (m, 2H), 7.58–7.46 (m, 3H), 7.27 (d, J=8.1 Hz, 2H), 7.03 (dd, J=7.8, 8.4 Hz, 1H), 5.99 (s, 1H), 4.55 (d, J=12.6 Hz, 1H), 4.02–3.82 (m, 3H), 3.79–3.43 (m, 4H), 3.54 (s, 3H), 3.53 (s, 3H), 2.79–1.51 (m, 13H).

HCl salt:
mp: 190.0–192.5° C.
$^1$H-NMR (DMSO-d$_6$): δ 10.65–10.37 (m, 1H), 9.36 (bv, 1H), 7.82–7.53 (m, 5H), 7.38 (d, J=8.1 Hz, 2H), 7.19 (t, J=8.1 Hz, 1H), 5.93 (s, 1H), 4.56–2.70 (m, 12H), 3.47 (s, 3H), 3.40 (s, 3H), 2.15–1.22 (m, 8H).
IR (KBr): 3455, 1690, 1657, 1622 cm$^{-1}$.

Example 16

Dimethyl 4-(2,6-dichlorophenyl)-2-[4-(2,3,5,6-tetrahydro-4H-thiopyran4-yl)-piperazinyl]carbonylmethyl-6-phenylsulfinylmethyl-1,4-dihydropyridine-3,5-dicarboxylate, monohydrochloride This was prepared by a procedure similar to that described in Example 1-D, as a yellow solid.

free base:
$^1$H-NMR (CDCl$_3$): δ 8.13 (bv, 1H), 7.80–7.72 (m, 2H), 7.59–7.48 (m, 3H), 7.27 (d, J=8.1 Hz, 2H), 7.02 (t, J=8.1 Hz, 1H), 5.98 (s, 1H), 4.52 (d, J=12.6 Hz, 1H), 4.00–3.48 (m, 7H), 3.54 (s, 3H), 3.53 (s, 3H), 2.77–2.28 (m, 9H), 2.18–2.03 (m, 2H), 1.79–1.57 (m, 2H).

HCl salt:
mp : 243.8–245.0° C. (decomposed) $^1$H-NMR (DMSO-d$_6$): 6 9.37 (bv, 1H), 7.80–7.70 (m, 2H), 7.68–7.53 (m, 3H), 7.38 (d, J=7.8 Hz, 2H), 7.19 (t, J=7.8 Hz, 1H), 5.93 (s, 1H), 4.53–2.30 (m, 19H), 3.40 (s, 3H), 3.33 (s, 3H), 1.88–1.63 (m, 2H).
IR (KBr): 3430, 3090, 2950, 1687, 1656, 1621 cm$^{-1}$.

Example 17

Dimethyl 4-(2.6-Dichlorophenyl)-2-[4-(8-methyl-8-azabicyclo[3,2,1]oct-3-yl)-1-piperazinyl]carbonylmethyl-6-[2-(phenylsulfinyl)ethyl]-1,4-dihydropyridine-3,5-dicarboxylate dihydrochloride A. Methyl 5-phenylthio-3-oxo-pentanoate To a suspension of NaH (60%) (815 mg, 20.39 mmol) in THF-HMPA (20 ml, 5 ml) was added methylacetoacetate (2.0 g, 18.5 mmol) in THF (5 ml) at 0° C. The mixture was stirred for 10 min. at 0° C. under nitrogen atmosphere. BuLi (12.3 ml, 20.39 mmol) was dropwise added and the red mixture was stirred for 15 min. at 0° C. Then a solution of chlorothioanisole (2.7 ml, 20.39 mmol) in THF (5 ml) was added to the mixture at 0° C. The mixture was stirred for 1 h at −5° C. The mixture was quenched with H$_2$O, then extracted with AcOEt (100 ml×2). AcOEt layer was washed with H$_2$O (10 ml×2) and brine (10 ml), then dried over MgSO$_4$ and evaporated. The residue was purified by a silica gel column chromatography (150 g, hexane :AcOEt=6:1) to give a colorless oil (1.0 g, 22.7%).

¹H-NMR (CDCl₃) δ 7.41–7.12 (m, 5H), 3.72 (S, 3H), 3.44 (s, 2H), 3.16 (t, J=7.3 Hz, 2H), 2.87 (t, J=7.3 Hz, 2H).

Benzylidene formation was made by a procedure similar to that described in 1-A as a colorless oil B. Dimethyl 4-(2,6-dichlorophenyl)-2-methoxycarbonylmethyl-6-(2-phenylthioethyl)-1,4-dihydropyridine-3,5-dicarboxylate This was prepared by a procedure similar to that described in 1-B as a pale yellow oil.

¹H-NMR (CDCl₃) δ 8.30 (bs, 1H), 7.69–7.42 (m, 5H), 7.31–7.12 (m, 2H), 7.05–6.90 (m, 1H), 5.97 (s, 1H), 4.00–3.38 (m), 3.69 (s, 3H), 3.51 (s, 3H), 3.45 (s, 3H), 3.38–3.19 (m), 3.19–2.94 (m).

C. Dimethyl 4-(2,6-dichlorophenyl)-2-[4-(8-methyl-8-azabicyclo[3,2,1]oct-3-yl)-1-piperazinyl]carbonylmethyl-6-[2-(phenylsulfinyl)ethyl]-1,4-dihydropyridine-3,5-dicarboxylate dihydrochloride Oxidation of the sulfide was made by a procedure similar to that described in 1-C as a 3:2 mixture of the diastereomers. Without separation of the diastereomers, the product was converted to the title compound (HCl salt) by a procedure similar to that described in 1-D as a pale yellow solid.

free base:
¹H-NMR (CDCl₃) δ 8.32 (bs, 1H), 7.72–7.40 (m, 5H), 7.32–7.10 (m, 2H), 7.06–6.87 (m, 1H), 5.96 (s, 1H), 4.18–3.31 (m), 3.51 (s, 1.8H), 3.50 (s, 1.2H), 3.47 (s, 1.8H), 3.46 (s, 1.2H), 3.31–2.95 (m), 2.94–2.72 (m), 2.27 (s, 1.2H), 2.21 (s, 3H), 1.78–1.39 (m).

HCl salt:
mp. 207.5–221° C.
¹H-NMR (DMSO) δ 11.90–11.41 (m, 1H), 10.92–10.06 (m, 1H), 9.50–9.11 (m, 1H), 7.76–7.48 (m, 5H), 7.40–7.22 (m, 2H), 7.18–7.03 (m, 1H), 5.80 (s, 1H), 3.39 (1.2H), 3.77 (s, 1.8H), 3.33 (s, 1.8H), 3.30 (s, 1.2H), 4.56–1.82 (m).
IR (KBr) 3430, 3335, 3250, 3205, 1703, 1688, 1669, 1651, 1085.

Preparation 1
Dimethyl 2-amino-1-propene-1,3-dicarboxylate

To a stirred solution of dimethyl acetonedicarboxylate (44.1 ml, 0.3 mole) and p-toluene-sulfonic acid (0.19 g, 1 mmol) in benzene (50 ml) was bubbled N-H₃ gas for 30 min. The mixture was refluxed with azeotropic removal of water using Dean-Stark trap. The bubbling of NH₃ gas and azeotropic removal of water was repeated three times. The reaction mixture was diluted with benzene and filtered through a celite pad. The filtrate was concentrated to give an amber color oil (50.75 g). The product was dissolved in diethylether (50 ml) and then hexane was added until the mixture became slightly turbit, and stirred slowly overnight to afford a white solid. This precipitate was collected by suction filtration and washed once with a 1:1 mixture of ether/hexane to give a white solid (44.55 g, 86%), mp 47–50° C.

¹H NMR (CDCl₃) δ 4.58 (s, 1H), 3.73 (s, 3H), 3.64 (s, 3H), 3.16 (s, 2H).

Preparation 2
1-(N-Methyl-8-azabicyclo[3,2,1]oct-3-yl)-piperazine
A. 1-Benzyl-4-(N-methyl-8-azabicyclo[3,2,1]oct-3-yl)-piperazine To a stirred solution of tropinone (5.00 g, 35.9 mmol) in dry methanol (115 ml) were added 1-benzylpiperazine (6.33 g, 35.9 mmol), activated powdered 3 molecular sieves (6.6 g) and sodium cyanoborohydride (4.75 g, 71.8 mmol). The reaction mixture was stirred at reflux under nitrogen atmosphere for 86 h. The reaction mixture was then filtered through a pad of celite. The filtrate was concentrated in vacuo. The resulting residue was then treated with 3 N aq. hydrochloric acid to pH ~1 under ice-bath cooling, and washed with ethyl acetate. The aqueous layer was then treated with 1 N aq. sodium hydroxide to pH 10, then extracted with CH₂Cl₂. The aqueous layer was then concentrated in vacuo and dried azeotropically with benzene. The resulting solid was extracted with 80 ml hot ethanol and insoluble materials were filtered off. This procedure was repeated to afford a dark brown oil (6.76 g). The oil was crystallized from methanolic hydrochloric acid solution (~1.3 N, 87 ml). The resulting precipitate was collected by suction filtration, washed with isopropyl alcohol, and dried in vacuo to afford a white solid (3.58 g). The CH₂Cl₂ phase obtained above was dried over anhydrous magnesium sulfate and concentrated in vacuo. The residue was mixed with the methanolic mother liquid above. The resulting precipitate was washed with isopropyl alcohol and dried in vacuo to afford a white solid (2.91 g). The combined products above (6.49 g) were dissolved in methanol (140 ml) and were treated with 1 N aq. sodium hydroxide to pH ~10. The whole was concentrated in vacuo and the resulting residue was dissolved in ethanol: CH₂Cl₂ solvent (1:10) and insoluble materials were filtered off. The filtrate was concentrated in vacuo to afford a pale yellow solid (4.75 g, 44% yield).

¹H-NMR (CDCl₃) δ 7.43–7.12 (m, 5H), 3.61–3.36 (m, 2H), 3.50 (s, 2H), 2.78–2.31 (m, 9H), 2.50 (s, 3H), 2.23–2.00 (m, 4H), 1.81–1.58 (m, 4H).

B. 1-(N-Methyl-8-azabicyclo[3.2.1]oct-3-yl)-piperazine

A solution of 1-benzyl-4-(N-methyl-8-azabicyclo[3,2,1] oct-3-yl)-piperazine (4.75 g, 15.88 mmol) in 50 ml methanol was hydrogenated at a pressure of 2.0 atm in the presence of 20% palladium hydroxide on carbon (470 mg) for 30 h. The mixture was then filtered through a pad of celite. The filtrate was concentrated to afford a pale yellow solid quantitatively, which is pure enough for subsequent use.

¹H-NMR (CDCl₃):s 3.33–3.16 (m, 2H), 2.97–2.78 (m, 4H), 2.65–2.40 (m, 5H), 2.31 (s, 3H), 2.10–1.91 (m, 2H), 1.84–1.68 (m, 2H), 1. 64–1.46 (m, 4H).

Preparation 3
1-(3-Quinuclidinyl)piperazine
A. 1-Benzyloxycarbonyl-4-(3-quinuclidinyl)-piperazine 3-Quinuclidinone hydrochloride (2.00 g, 97%, 12.0 mmol) dissolved in methanol (10 ml) were treated with 2 N aq. sodium hydroxide (6 ml) at room temperature. The mixture was concentrated in vacuo and the residue was dried azeotropically with ethanol. The residue was dissolved in ethanol (20 ml) and insoluble materials were removed by suction filtration. The filtrate was concentrated in vacuo to afford a white solid (1.476 g). This solid and 1-benzyloxypiperazine (2.64 g, 12.0 mmol) were dissolved in dry methanol (33 ml). To the stirred solution was added activated powdered 3 angstrom molecular sieves (2.2 g), and sodium cyanoborohydride (1.58 g, 24.0 mmol). The mixture was stirred at room temperature for 16 h. The reaction mixture was then filtered through a pad of celite. The filtrate was concentrated in vacuo. The resulting residue was quenched with water and then 6 N aq. hydrochloric acid to pH ~1 under ice-bath cooling. The whole was washed with ethyl acetate and the aqueous layer was concentrated in vacuo. The residue was dissolved in methanol and treated with aq. sodium carbonate solution to pH ~11. The whole was concentrated and dried azeotropically with isopropyl alcohol. The residue was dissolved in ethanol and the insoluble materials were removed by suction filtration. The filtrate was concentrated in vacuo to afford 2.04 g of a yellow oil. Chromatography on silica gel (40 g) eluted with CH$_2$Cl$_2$:MeOH=100:1 to 10:1(+1% Et$_3$N) afforded a pale yellow oil (728 mg 18% yield).

$^1$H-NMR (CDCl$_3$) δ 7.42–7.26 (m, 5H), 5.13 (s, 2H), 3.60–3.42 (m, 4H), 3.08–2.60 (m, 7H),2.47–2.26 (m, 4H), 2.07–1.93 (m, 2H), 1.87–1.61 (m, 1H), 1.52–1.21 (m, 2H).

B. 1-(3-Quinuclidinyl)piperazine

A solution of 1-benzyloxy-4-(3-quinuclidinyl)piperazine (728 mg, 2.21 mmol) in methanol (5 ml). was hydrogenated at an atmospheric pressure in the presence of 10% palladium on carbon (73 mg) at room temperature for 15 h. The mixture was then filtered through a pad of celite. The filtrate was concentrated to afford a white solid (423 mg, 98% yield).

$^1$H-NMR (CDCl$_3$) δ 4.37–4.13 (m, 1H), 3.10–2.63 (m, 1H), 2.54–2.28 (m, 4H), 2.11–1.95 (m, 2H), 1.90–1.63 (m, 1H), 1. 56–1.23 (m, 2H).

Preparation 4
(3-Hydroxy-bicyclo[3.3.0]oct-7-yl)piperazine

Reductive amination with bicyclo[3,3,0]octa-3,7-dione (4.1 g, 29.3 mmol) under a similar condition as shown in preparation 2. Recrystallization from isopropyl alcohol/diisopropyl ether afforded a white solid (2.5 g, 49%). The product (1.38 g, 6.57 m mol) was converted to the corresponding hydrochloric salt and recrystallized from isopropanol gave a white solid (567 mg, 30% yield).

$^1$H-NMR (D$_2$O) δ 4.42–4.27 (m, 1H), 3.85–3.48 (m, 9H), 2.65–2.42 (m, 4H), 2.21–2.06 (m, 2H), 1.83–1.48 (m, 4H).

In addition, the chemical structure of the compounds prepared in the examples are summarized in the following Table.

TABLE (I)

| Ex. # | X | A$^1$ | A$^2$ | R$^1$ |
|---|---|---|---|---|
| 1 | S(O) | Cl | Cl | 8-methyl-8-azabicyclo[3.2.1]oct-3-yl |
| 2 | C(O) | Cl | Cl | 8-methyl-8-azabicyclo[3.2.1]oct-3-yl |
| 3 | C(O) | Cl | Cl | quinuclidin-3-yl |
| 4 | C(O) | Cl | Cl | 3-hydroxy-bicyclo[3.3.0]oct-7-yl |
| 5 | S(O) | Cl | Cl | [1-(hydroxy) cyclopentyl]ethyl |
| 6 | S(O)$_2$ | Cl | Cl | 8-methyl-8-azabicyclo[3,2,1]octan-3-yl |
| 7 | S(O) | Cl | Cl | 3-hydroxy-bicyclo[3,3,0]oct-7-yl |
| 8 | S(O) | Cl | Cl | cycloheptyl |
| 9 | S(O) | Cl | Cl | cyclohexyl |
| 10 | S(O) | Cl | Cl | cyclooctyl |
| 11 | S(O) | Cl | Cl | 3-oxo-bicyclo[3,3,0]oct-7-yl |
| 12 | S(O) | Cl | Cl | cis-1,5-dimethyl-3-oxo-bicyclo[3,3,0]oct-7-yl |
| 13 | S(O) | Cl | Cl | 5-oxo-cyclooctyl |
| 14 | S(O) | Cl | Cl | 1,4-dioxaspiro[4,5]dec-8-yl |
| 15 | S(O) | Cl | Cl | 4-oxo-cyclohexyl |

TABLE-continued

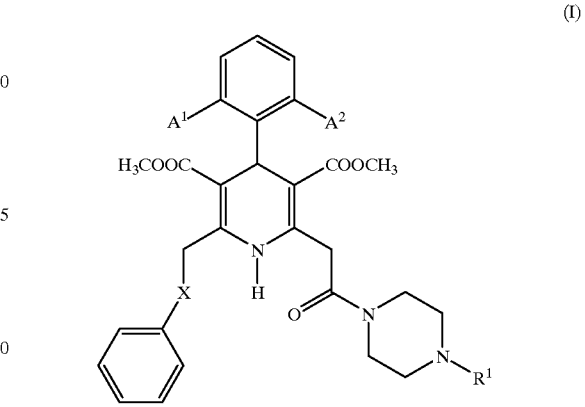

| Ex. # | X | A$^1$ | A$^2$ | R$^1$ |
|---|---|---|---|---|
| 16 | S(O) | Cl | Cl | 2,3,5,6-tetrahydro-4H-thiopyran-4-yl |
| 17 | S(O)-methyl | Cl | Cl | 8-methyl-8-azabicyclo[3,2,1]oct-3-yl |

What is claimed is:

1. A compound of the formula:

(I)

and its pharmaceutically acceptable salts, wherein A$^1$ and A$^2$ are each halo; X is CO, S(O)$_2$ or S(O)—(CH$_2$)n wherein S atom is directly attached to the phenyl and n is 0, 1 or 2; and R$^1$ is 8-azabicyclo[3.2.1]octyl, quinuclidinyl, bicyclo[3.3.0]octyl, C$_{3-10}$ cycloalkyl, 2,3,5,6-tetrahydro-4H-thiopyranyl or C$_{3-6}$ cycloalkyl-C$_{1-4}$ alkyl, optionally substituted with C$_{1-4}$ alkyl, hydroxy, dioxolanespiro or oxo.

2. A compound according to claim 1, wherein A$^1$ and A$^2$ are chloro.

3. A compound according to claim 2, wherein R$^1$ is 8-methyl-8-azabicyclo[3.2.1]oct-3-yl, quinuclidin-3-yl, 3-hydroxy-bicyclo[3.3.0]oct-7-yl, [1-(hydroxy) cyclopentyl]ethyl or 3-oxo-bicyclo[3,3,0]oct-7-yl.

4. A compound according to claim 1, being one of the following:

dimethyl 4-(2,6-dichlorophenyl)-2-[4-(8-methyl-8-azabicyclo[3.2.1]oct-3-yl)-1 -piperazinyl]carbonylmethyl-6-phenylsulfinylmethyl-1,4-dihydropyridine-3,5-dicarboxylate dihydrochloride;

dimethyl 4-(2,6-dichlorophenyl)-2-[4-(8-methyl-8-azabicyclo[3.2.1]oct-3-yl)-1-piperazinyl]carbonylmethyl-6-(2-oxo-2-phenylethyl)-1,4-dihydropyridine-3,5-dicarboxylate dihydrochloride;

dimethyl 4-(2,6-dichlorophenyl)-(2-oxo-2-phenylethyl)-2-[4-(3-quinuclidinyl)-1-piperazinyl]carbonylmethyl-1,4-dihydropyridine-3,5-dicarboxylate dihydrochloride;

dimethyl 4-(2,6-dichlorophenyl)-(2-oxo-2-phenylethyl)-2-[4-(3-hydroxy-bicyclo[3.3.0]oct-7-yl)piperazin-1-yl]carbonylmethyl-1,4-dihydropyridine-3,5-dicarboxylate hydrochloride;

dimethyl 4-(2,6-dichlorophenyl)-2-{2-[1-(hydroxy)cyclopentyl]ethylpiperazinyl} carbonylmethyl-6-phenylsulfinylmethyl-1,4-dihydropyridine-3,5-dicarboxylate;

dimethyl 4-(2,6-dichlorophenyl)-2-[4-(8-methyl-8-azabicyclo[3,2,1]octan-3-yl)-1-piperazinyl]carbonylmethyl-6-(phenylsulfinylmethyl-1,4-dihydropyridine-3,5-dicarboxylate dihydrochloride;

dimethyl 4-(2,6-dichlorophenyl)-2-[4-(3-hydroxy-bicyclo[3,3,0]oct-7-yl)-1-piperazinyl]carbonylmethyl-6-(phenylsulfinylmethyl-1,4-dihydropyridine-3,5-dicarboxylate monohydrochloride;

dimethyl 4-(2,6-dichlorophenyl)-2-[4-(3-oxo-bicyclo[3,3,0]oct-7-yl)piperazinyl]-carbonylmethyl-6-phenylsulfinylmethyl-1,4-dihydropyridine-3,5-dicarboxylate, monocitric acid;

dimethyl 4-(2,6-dichlorophenyl)-2-[4-(cis-1,5-dimethyl-3-oxo-bicyclo[3,3,0]oct-7-yl)-piperazinyl]carbonylmethyl-6-phenylsulfinylmethyl-1,4-dihydropyridine-3,5-dicarboxylate, monohydrochloride; and dimethyl 4-(2,6-dichlorophenyl)-2-[4-(5-oxo-cyclooctyl)-piperazinyl]carbonylmethyl-6-phenylsulfinylmethyl-1,4-dihydropyridine-3,5-dicarboxylate, monohydrochloride.

5. A compound according to claim 4, being one of the following:

dimethyl 4-(2,6-dichlorophenyl)-2-[4-(8-methyl-8-azabicyclo[3.2.1]oct-3-yl)-1-piperazinyl]carbonylmethyl-6-phenylsulfinylmethyl-1,4-dihydropyridine-3,5-dicarboxylate dihydrochloride;

dimethyl 4-(2,6-dichlorophenyl)-2-[4-(8-methyl-8-azabicyclo[3.2.1]oct-3-yl)-1-piperazinyl]carbonylmethyl-6-(2-oxo-2-phenylethyl)-1,4-dihydropyridine-3,5-dicarboxylate dihydrochloride;

dimethyl 4-(2,6-dichlorophenyl)-(2-oxo-2-phenylethyl)-2-[4-(3-quinuclidinyl)-1-piperazinyl]carbonylmethyl-1,4-dihydropyridine-3,5-dicarboxylate dihydrochloride; and dimethyl 4-(2,6-dichlorophenyl)-(2-oxo-2-phenylethyl)-2-[4-(3-hydroxy-bicyclo[3.3.0]oct-7-yl)piperazin-1-yl]carbonylmethyl-1,4-dihydropyridine-3,5-dicarboxylate hydrochloride.

6. A compound according to claim 5, dimethyl 4-(2,6-dichlorophenyl)-2-[4-(8-methyl-8-azabicyclo[3.2.1]oct-3-yl)-1-piperazinyl]carbonylmethyl-6-phenylsulfinylmethyl-1,4-dihydropyridine-3,5-dicarboxylate dihydrochloride; or dimethyl 4-(2,6-dichlorophenyl)-2-[4-(8-methyl-8-azabicyclo[3.2.1]oct-3-yl)-1-piperazinyl]carbonylmethyl-6-(2-oxo-2-phenylethyl)-1,4-dihydropyridine-3,5-dicarboxylate dihydrochloride.

7. A pharmaceutical composition for the treatment of inflammation, cardiovascular disease, pain, common cold, allergies, asthma, pancreatitis, burns, virus infection, head injury, multiple trauma, which comprises a therapeutically effective amount of a compound of claim 1 and a pharmaceutically acceptable carrier.

8. A method for the treatment of disease conditions caused by bradykinin, in a mammalian subject, which comprises administering to said subject a therapeutically effective amount of a compound according to claim 1.

* * * * *